United States Patent [19]
Mizutani

[11] Patent Number: 5,792,131
[45] Date of Patent: Aug. 11, 1998

[54] INDIVIDUALLY WRAPPED SANITARY NAPKIN

[75] Inventor: Satoshi Mizutani, Ehime-ken, Japan

[73] Assignee: Uni-Charm Corporation, Ehime-ken, Japan

[21] Appl. No.: 674,234

[22] Filed: Jun. 28, 1996

[30] Foreign Application Priority Data

Jun. 30, 1995 [JP] Japan .................. 7-166030

[51] Int. Cl.$^6$ .................................. A61F 13/15
[52] U.S. Cl. .................. 604/385.1; 604/389; 604/390; 206/438
[58] Field of Search .............. 604/388.1, 385.2, 604/386, 387, 389, 390; 206/440, 438

[56] References Cited

U.S. PATENT DOCUMENTS

| | | | |
|---|---|---|---|
| H1454 | 6/1995 | Cucuzza et al. | 604/385.1 |
| 3,963,029 | 6/1976 | Brooks | 604/385.1 |
| 4,781,712 | 11/1988 | Barabino et al. | 604/385.1 |
| 5,088,993 | 2/1992 | Gaur | 604/385.1 |
| 5,413,568 | 5/1995 | Roach et al. | |
| 5,462,166 | 10/1995 | Minton et al. | |
| 5,569,228 | 10/1996 | Byrd et al. | 604/385.1 |
| 5,569,230 | 10/1996 | Fisher et al. | 604/385.1 |

FOREIGN PATENT DOCUMENTS

| | | |
|---|---|---|
| 57-34211 | 2/1982 | Japan . |
| 57-57828 | 4/1982 | Japan . |

*Primary Examiner*—Mark O. Polutta
*Attorney, Agent, or Firm*—Lowe Hauptman Gopstein Gilman & Berner

[57] ABSTRACT

An individually wrapped sanitary napkin comprising a sanitary napkin folded with a back surface thereof lying outside and with one of longitudinally opposite ends underlying the other end thereof and a wrapping sheet folded so as to wrap the napkin with one of longitudinally opposite ends underlying the other end thereof. A portion of the wrapping sheet is integrally fastened at a predetermined region to an outer surface of a releasable sheet protectively covering an adhesive zone on the back surface of the napkin. The longitudinal one end of the wrapping sheet is releasably fastened to an outer surface of the portion of the wrapping sheet which has been integrally fastened to the releasable sheet. Such a feature allows the longitudinal one end of the wrapping sheet to stand repeated manipulations of stripping away from and fastening to the outer surface of the integrally fastened portion.

4 Claims, 2 Drawing Sheets

INDIVIDUALLY WRAPPED SANITARY NAPKIN

TECHNICAL FIELD

The present invention relates to an individually wrapped sanitary napkin and, more particularly, a sanitary napkin or menstruation pad which is folded and individually wrapped by a wrapping sheet.

BACKGROUND ART

Conventional individually wrapped sanitary napkins are folded in thirds with a back surface thereof outwardly disposed and with one longitudinal end thereof underlying the opposite longitudinal end. The conventional napkins are then wrapped by a wrapping sheet constructed in the form of an envelope having a flap extending from an opening thereof. Such wrapped sanitary napkins are disclosed in Japanese Laid-Open Utility Model Applications Nos. Sho57-57828 and Sho57-34211, in which the flap is releasably bonded, by adhesive means provided on an inner surface thereof, to an outer surface of the envelope's body to close the opening of the envelope.

However, a disadvantage of the foregoing wrapped sanitary napkins is that the envelope will be often torn or unduly extended as the flap is peeled off the envelope's body to open the envelope if the envelope is constructed of a thin flexible plastic film.

Accordingly, a principal object of the invention is to provide an individually wrapped sanitary napkin to solve such a problem.

DISCLOSURE OF THE INVENTION

According to the invention, there is provided an individually wrapped sanitary napkin comprising a longitudinally elongated sanitary napkin and a wrapping sheet dimensioned larger than the napkin. The napkin has on a wearer's skin-noncontacting surface of the napkin an adhesive zone to fasten the napkin to a wearer's pants and a releasable sheet for protectively covering the adhesive zone. The napkin is folded up longitudinally in thirds with the releasable sheet lying outside and wrapped with the wrapping sheet in such a manner that a longitudinally intermediate section of the wrapping sheet covers a longitudinally intermediate section of the wearer's skin-noncontacting surface of the napkin. Longitudinally opposite ends of the wrapping sheet respectively lie adjacent longitudinally opposite ends of the wearer's skin-noncontacting surface of the napkin and the wrapping sheet overlaps itself.

The present invention includes one of the wrapping sheet's longitudinally opposite ends directly overlapping itself from outside. One end of the wrapping sheet is releasably fastened to an outer surface of the wrapping sheet at a region underlying the one end by means of an adhesive zone provided on an inner surface of the one end. A portion of the releasable sheet underlying a portion of the wrapping sheet is defined by the adhesive zone and the portion of the releasable sheet is integrally fastened to an inner surface of the wrapping sheet.

With the individually wrapped sanitary napkin constructed as described above, the one end of the wrapping sheet can be repeatedly stripped away from and fastened to the outer surface of the wrapping sheet, since the one end of the wrapping sheet is releasably fastened to the outer surface of the wrapping sheet at the fastening region at which the wrapping sheet has been fastened to the release sheet.

BEST MODE FOR CARRYING OUT THE INVENTION

Figure 1:
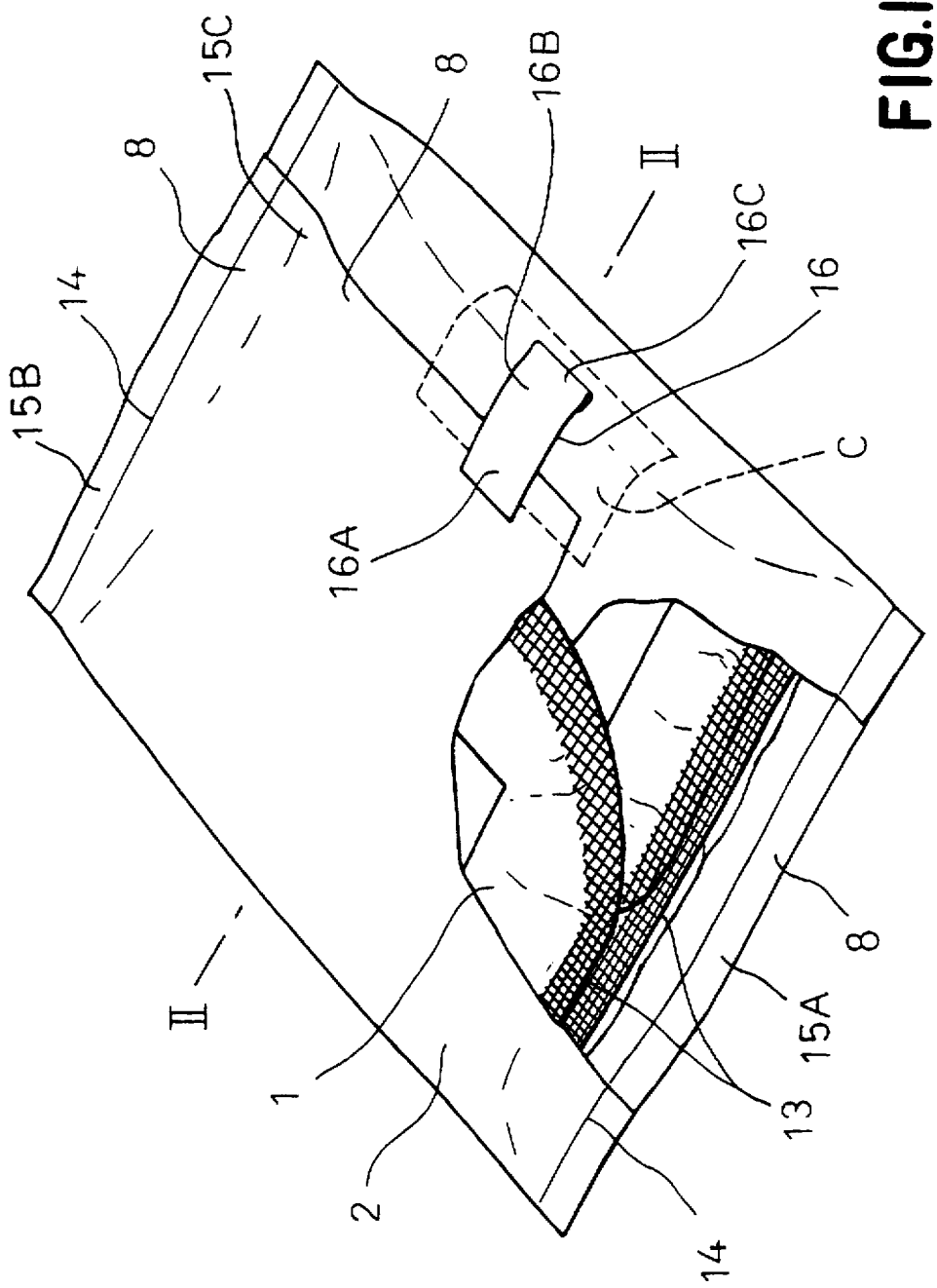
FIG. 1 is a perspective view depicting an individually wrapped sanitary napkin as partially broken away.
Figure 2:
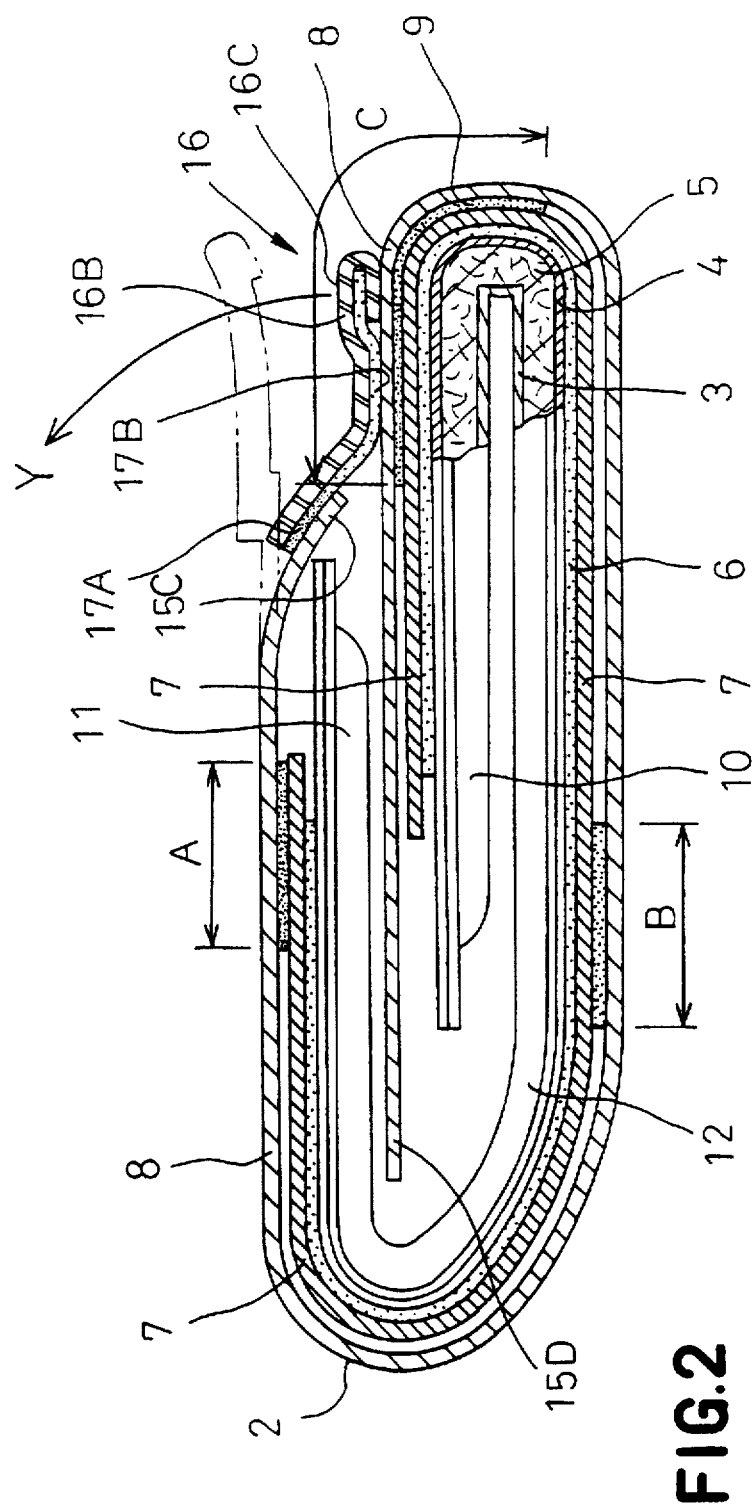
FIG. 2 is a sectional view taken along a line II—II in FIG. 1.

Referring to FIGS. 1 and 2, an individually wrapped sanitary napkin comprises a sanitary napkin 1 and an individual wrap 2. Sanitary napkin 1 is longitudinally elongated and comprises a liquid-permeable topsheet 3 made of a nonwoven fabric and defining a wearer's skin-contacting surface, a liquid-impermeable backsheet 4 made of a plastic film and defining a wearer's skin-noncontacting surface and a liquid-absorbent core 5 formed by a mixture of fluff pulp and superabsorbent polymer particles and disposed between the top sheet 3 and the backsheet 4. An outer surface of the backsheet 4 is applied with adhesive 6 by means of which the backsheet 4 is fastened to a wearer's pants and the adhesive 6 is protectively covered with a releasable paper sheet 7. An outer surface of the releasable sheet 7 is covered with a wrapping sheet 8 made of a thin flexible plastic film which is dimensioned larger than the napkin 1 so that transversely opposite marginal areas 15A, 15B and longitudinally opposite marginal areas 15C, 15D of the wrapping sheet may extend from a peripheral edge of the napkin 1 and be fastened at desired regions. For example, areas A, B and C as depicted in FIG. 2, are fastened to the wrapping sheet 8 by means of hotmelt adhesive 9. The napkin 1 assembled in this manner is now folded in thirds with the topsheet 2 lying inside and with longitudinally opposite ends 10, 11 of the napkin 1 being placed one upon the other.

The napkin 1 has, in its folded up state, an inner end section 10, an outer end section 11 and an intermediate section 12 extending between the two end sections 10, 11. Portions of the wrapping sheet 8 extend outward beyond transversely opposite edges 13 of the napkin 1 and are heat-sealed along a pair of seal-lines 14. One end 16A of a pick-out tab 16 formed by a relatively narrow plastic film strip is fastened to the marginal area 15C of the wrapping sheet 8 adjacent the outer end section 11 of the napkin 1 at a transversely middle area of the marginal area 15C by means of adhesive 17A. A free end 16B of the tab 16 extending outward beyond the marginal area 15C is applied on its inner surface with adhesive 17B so that the free end 16B is releasably fastened to an outer surface of the wrapping sheet 8 at the area C. In this manner, the napkin 1 is wrapped by the wrapping sheet 8. A forward end of the tab 16 is folded back and fastened to its own inner surface to form a non-adhesive pick-out tip 16C.

With the individually wrapped sanitary napkin constructed as described above, the pick-out tip 16C of the tab 16 may be held between a wearer's fingers and pulled in a direction indicated by an arrow Y (see FIG. 2) to strip the tab 16 away from the area C of the wrapping sheet. The tab 16 may be further pulled to tear the wrapping sheet 8 along the seal-lines 14 whereby to strip the releasable sheet 7 away from the napkin 1. If it is necessary to interrupt the stripping operation for any reason, the adhesive 6 will be protected by the releasable sheet 7 and the tab 16 may be fastened again to the wrapping sheet 8 at the area C to prevent the napkin 1 from being contaminated with dust or the like. Even if the manipulation of stripping away from and fastening to the wrapping sheet 8 is repeated, the wrapping sheet 8 will not be easily torn or unduly extended, since the wrapping sheet 8 is integrated at the area C with the releasable sheet 7 by means of adhesive 9. The wrapping sheet 8 is preferably finely wrinkled at the area C, since such fine wrinkles will advantageously reduce an effective area over which the tab 16 is fastened to the wrapping sheet 8 at the area C so that the tab 16 can be stripped away therefrom with a relatively small force of stripping and the wrapping sheet 8 can be reliably prevented from being torn or unduly extended at the area C.

While it is also possible in this individually wrapped sanitary napkin to fasten the marginal area 15 of the wrapping sheet 8 directly to itself at the area C without use of the tab 16, preferably an additional film having both a tear strength and a rigidity higher than the wrapping sheet 8 is used as the tab 16 to implement the invention.

With the individually wrapped sanitary napkin of the invention, the areas of the wrapping sheet integrally fastened to the releasable sheet are not easily broken, torn, or unduly extended, so the marginal area of the wrapping sheet releasably fastened to itself at the regions can withstand repeated manipulations of fastening to and stripping away from the wrapping sheet.

What is claimed is:

1. An individually wrapped sanitary napkin comprising:
    an elongated sanitary napkin including a skin-contacting surface, a skin-noncontacting surface and an absorbent core disposed between the two surfaces, wherein the skin-contacting surface comprises a liquid permeable topsheet and the skin-noncontacting surface comprises a liquid impermeable backsheet, the skin-noncontacting surface including a first adhesive zone for fastening said napkin to an undergarment and a releasable sheet for protectively covering said first adhesive zone; and a wrapping sheet dimensioned larger than said napkin, wherein said napkin is folded along at least one axis that is traverse to a longitudinal axis of said napkin with said releasable sheet lying inside and being wrapped with said wrapping sheet; said wrapping sheet having a first end and a second end, said skin-noncontacting surface of said napkin having a first end and a second end lying adjacent to the first end and the second end of said wrapping sheet respectively, wherein the first end of said wrapping sheet overlaps the second end of said wrapping sheet and the first end is releasably fastened to an outer surface of the second end of said wrapping sheet at a fastening region, a portion of said wrapping sheet underlying the fastening region is attached to a portion of said releasable sheet by a second adhesive zone provided therebetween.

2. An individually wrapped sanitary napkin according to claim 1, wherein an outer surface of the portion of said wrapping sheet defined by said second adhesive zone as the fastening region is formed with fine wrinkles.

3. An individually wrapped sanitary napkin according to claim 1, wherein said wrapping sheet is made of a plastic film.

4. An individually wrapped sanitary napkin according to claim 1, wherein the portion of said releasable sheet is integrally fastened to an inner surface of said wrapping sheet.

* * * * *